United States Patent [19]

Bisconte

[11] Patent Number: 4,800,164
[45] Date of Patent: Jan. 24, 1989

[54] AUTOMATIC DEVICE FOR THE ANALYSIS AND CLONING OF CELLULAR CULTURES AS WELL AS FOR BACTERIOLOGICAL ANALYSIS

[75] Inventor: Jean-Claude Bisconte, Paris, France

[73] Assignee: Institut National de la Sante et de la Recherche Medicale-INSERM, Paris, France

[21] Appl. No.: 751,248

[22] Filed: Jul. 2, 1985

[30] Foreign Application Priority Data

Jul. 12, 1984 [FR] France ............... 84 11073

[51] Int. Cl.$^4$ ............................................. C12M 1/18
[52] U.S. Cl. .................................. 435/300; 435/313
[58] Field of Search ............... 435/291, 292, 287, 293, 435/294, 300, 301, 311, 808, 284, 286; 422/67, 100, 63, 104, 64, 65; 356/244; 414/1

[56] References Cited

U.S. PATENT DOCUMENTS

| | | | |
|---|---|---|---|
| 3,106,090 | 10/1963 | Barnes | 435/300 |
| 3,322,956 | 5/1963 | Shah | 250/564 |
| 3,501,379 | 3/1970 | Tate | 435/300 |
| 3,773,426 | 11/1973 | Mudd | 356/205 |
| 4,090,921 | 5/1978 | Sawamura et al. | 435/284 |
| 4,235,971 | 11/1980 | Howard et al. | 435/293 |
| 4,250,266 | 2/1981 | Wade | 435/289 |
| 4,339,537 | 7/1982 | Sogi et al. | 435/286 |
| 4,442,387 | 4/1984 | Lindbom | 414/1 |
| 4,480,031 | 10/1984 | Shaw | 435/292 |
| 4,613,573 | 9/1986 | Shibayama et al. | 435/311 |
| 4,626,509 | 12/1986 | Lyman | 435/287 |
| 4,696,902 | 9/1987 | Bisconte | 435/300 |
| 4,711,851 | 12/1987 | McNamara et al. | 435/287 |

FOREIGN PATENT DOCUMENTS

| | | |
|---|---|---|
| 1577539 | 5/1968 | France . |
| 2250991 | 6/1975 | France . |
| 2424961 | 11/1979 | France . |
| 2633085 | 1/1977 | Japan . |
| 2945339 | 5/1980 | Japan . |
| 926541 | 5/1963 | United Kingdom . |
| 1112919 | 6/1968 | United Kingdom . |

Primary Examiner—James C. Yeung
Attorney, Agent, or Firm—Browdy & Neimark

[57] ABSTRACT

An automatic device for analyzing and cloning cellular cultures and bacteriological analysis, comprising an enclosure divided into two compartments, the first compartment of which contains: a circular transparent plate comprising several microwells disposed in one or more circular concentric rows, at least one special microscopic observation device, more especially of the phase contrast type, a device for the aspiration/injection of cellular medium or cells guaranteeing non contamination, a motor unit for providing the rotational as well as vertical and horizontal movements of said plate, with very accurate positioning in the three directions of movement, whereas the second compartment surrounds the first one and contains the regulation devices, and a cooling block containing the nutritive medium supply reservoirs. The automatic device is controlled by a microprocessor. The device of the present invention may be applied to the analysis and cloning of cellular cultures as well as for bacteriological analysis.

32 Claims, 5 Drawing Sheets

AUTOMATIC DEVICE FOR THE ANALYSIS AND CLONING OF CELLULAR CULTURES AS WELL AS FOR BACTERIOLOGICAL ANALYSIS

BACKGROUND OF THE INVENTION

1. Field of the Invention

The present invention relates to an automatic device for analysing and cloning cellular structures, as well as for bacterial analysis, namely an apparatus integrating the phases of maintenance and experimentation of substances, particularly pharmacological, of the optical analysis of the density and the form of cells, as well as associations thereof, and of the pricking out of the adherent cells with a view to cloning same.

2. Description of the Prior Art

At the present time, cell culture on a support medium is carried out in standardized containers such as Petri boxes, multihole boxes, or flasks. The morphological analysis of living cells, generally carried out with a phase contrast reversed microscope, aims at counting the cells, detecting the presence of colonies, studying the spontaneous or provoked differenciation of the cells, or else following the evolution of their form and of their movement by time-lapse cinematography.

These observations are of very great interest in studying the growth and normal or experimental differenciation of cells, in particular for following up the effects of drugs, hormones, toxic products. The use of the present containers involves carrying out phases forming a sequence of dissociated operations, with passage through various devices, such as wet $CO_2$ incubators for storage, lamina flow tanks for renewing the media or for cell handling, reversed microscope coupled or not to an image forming device (video camera or photographic camera).

Several microscope constructors propose thermostat controlled enclosures comprising a reversed microscope.

There exist moreover motor driven plates and image analysis devices.

In 1980 the inventor showed (MIKROSCOPIE) the use of video image analysis, associated with a thermostat controlled enclosure and with motor driven plates, for following up cell kinetics.

Such large volume devices, associating conventional components, may comprise $CO_2$ content regulation, but it is not advisable to create water saturation which would inevitably cause zones of condensation and would be a source of contamination, but more especially of rapid deterioration of the optical systems and of the micro-mechanics. Thus, the rapid evaporation which results therefrom limits the duration of analysis sequences to a few hours and to 48 hours at most.

In addition, the complex forms of the devices included in the enclosure are not appropriate to maintaining sterility.

At the present time, these enclosures which include a microscope allow the evolution of cultures to be followed maintained in the wells of a box, but the analysis of several boxes in a limited time, and all the more so long term analysis, i.e. including operations for changing nutritive medium, are not possible in an automated way.

The inventor has further proposed an original solution for the long term maintenance and analysis of culture boxes of conventional shapes (cf. French patent application No. 84 08839).

When the maintenance, sampling and cell analysis operations are not longterm operations, do not use a very large number of samples and do not present great risks of contamination for man, it is advantageous to design an apparatus strictly adapted and optimized in all its components.

SUMMARY OF THE INVENTION

The first aim of the invention is to eliminate these drawbacks, in particular in so far as is concerned the limited analysis time, the restricted number of small boxes which can be treated and of the fields of observation which may be determined, as well as the risks of contamination.

Another aim of the invention is to provide an original apparatus which integrates operations which have up to now being dissociated, more particularly in so far as automatic cloning is concerned.

Another aim of the invention is to provide a single and self contained apparatus which is relatively inexpensive and which does not require investment in rooms and specialized equipment.

Another aim of the invention is to approximate optimum conditions by completely eliminating thermal and mechanical shocks, and by providing uniform culture conditions independently of the operator.

Another aim of the invention is to allow the environmental conditions of the cells, including the nutritive medium, to be made dependent, by means of software, on parameters measured frequently or even continuously.

The present invention provides a very compact automatic apparatus for analysing and cloning cellular cultures, as well as for bacteriological analysis, namely an apparatus integrating the phases of maintenance, experimentation of substances particularly pharmacological, optical analysis of the density and of the form, as well as associations thereof, and the sub-culture of cells with a view to cloning same, characterized in that it comprises in combination:

an enclosure with isolating walls, providing homeothermic conditions and certain environmental conditions, particularly in terms of hygrometry, percentage of $CO_2$ and/or others, inside this enclosure, which is divided into two compartments, the first compartment of which is small in volume and contains:

- a plate, preferably circular, comprising several microwells disposed in one or more circular concentric rows, the plate and the microwells being made from a transparent material having good optical qualities,
- at least one special microscopic observation device, particularly of the phase contrast type,
- a device for aspiring/injecting the cellular medium or cells, guaranteeing non contamination;
- a motor unit for driving the plate in rotation and vertical and horizontal movements with very accurate positioning in the three directions of movement, whereas the second compartment of the enclosure, which surrounds the first compartment except at the level of the front face of the enclosure, contains a device for regulating the temperature and stirring the hot air and, possibly, a device for sterilizing the first compartment by a flow of filtered laminar air in a closed circuit, known per se, said first and second compartments being separated by a wall, possibly filtering, for allowing the possible laminar flow to circulate between these two compartments, and a cooling block disposed inside the enclosure thus equipped, containing in particular the reservoirs for supplying the nutritive media and different products.

In an advantageous embodiment of the automatic device of the invention, said plate is provided with a central opening for access of said aspiration/injection device, which is fixed to the upper wall of the first compartment, into a discharge and sterilization well fixed to the lower wall of this compartment.

In another advantageous embodiment of the automatic device in accordance with the invention, said circular plate is placed in a cassette, more especially metallic and substantially square in shape which, when it is equipped with a lid, has a configuration close to that of the Petri box for reducing the risks of contamination and which comprises a central circular recess for housing the plate which, in the rest position, is held in place by support means preferably formed by four balls housed in the wall of said recess and projecting from this latter for snapping into an annular groove formed in the outer wall of the plate, whereas the rotational drive of the plate is formed by a drive roller, projecting from said motor unit, by engagement under the action of appropriate means and by friction in the groove of the plate, an access window of the roller into this groove being formed for this purpose in the middle part, on the same side of the cassette adjacent the motor unit.

In an advantageous arrangement of this embodiment, two of said balls are fixed whereas the other two balls are on a resilient support, more particularly a spring support, the four balls being disposed at the apices of a square inscribed in the circumference defining said circular recess, so that one side of the square, parallel and contiguous to said access window of the drive roller, is defined by the fixed balls, whereas the opposite side of the square is defined by said two balls on the resilient support so that, when the roller engages in said groove, these latter balls only participate in the rotational guiding of the plate, the two fixed balls being freed from the groove thereof;

In another advantageous arrangement of this embodiment said means allowing the drive roller to engage in the groove of the plate are formed by an electromagnet providing the flexible coupling between the opposite metal walls of the drive unit and the cassette.

In another advantageous arrangement of this embodiment, the support cassette is provided with a transparent lid, of good optical quality, fitted to said central opening in the plate and having a radial window for access of said aspiration/injection device into the microwells of the plate.

Also in accordance with the invention, balls disposed on the side walls and on the lower and upper walls of the cassette allow this support cassette to slide freely.

Further in accordance with the invention, said support cassette is sterilizable, as well as the plate and the lid.

In a preferred embodiment of the automatic device of the invention, this latter cooperates with a plurality of plates, each contained in a cassette of said type, so as to store the cassettes in an incubator apart and only to introduce into said first compartment the cassette corresponding to a certain experimental protocol.

In accordance with yet another advantageous embodiment of the automatic device of the invention, said motor unit comprises in combination:

a first stepper motor for rotating said plate which acts on the drive roller through a step down system, a second stepper motor which ensures the horizontal movement of the plate by acting on a gear system which projects from the motor unit and which acts in its turn on at least one rack fixed to the lower wall of the first compartment, and a third stepper motor for the unilateral adjustment of the height of the plate, which acts on a micrometric screw disposed laterally with respect to said drive roller and having at its lower end a ball bearing sliding over the lower wall of said first compartment, so as to allow the horizontal movements operated by said second stepper motor.

According to an advantageous embodiment of the automatic device of the invention, said microscopic observation device comprises two preset lens/condenser pairs which are associated together and which are intended to operate alternately, the first and second condensers and the first and second lenses being fixed to the ceiling and the floor, respectively, of the separation wall between said two compartments of the enclosure, which first lens is of low magnification, whereas the second lens provides medium or high magnification depending on the needs, the light being input into the two condensers by means of an optical fiber system.

In an advantageous arrangement of this embodiment, each lens cooperates with a mirror and an image sensor formed by a TV camera or by a CCD strip coupled or not to an automatic image analyser.

According to another advantageous feature of this arrangement, the intermediate mirror, which is interposed between said image sensor and the mirror the furthest away therefrom, is semi-transparent.

In an advantageous variant of this feature, said intermediate mirror is retractable, more especially under the action of an electromagnet system, when the lens/condenser pair the furthest away from the image sensor is activated.

In another advantageous embodiment of the automatic device of the invention, the aspiration/injection device is disposed in a vertical housing formed in the upper wall of the first compartment and cooperates with a device for setting the aspiration/injection nozzle in three positions, formed more especially by a stepper motor or by a telescopic actuating cylinder, for:

in the top position, causing the support cassette as well as the plate to move freely, in the intermediate position, to aspirate impoverished cellular medium or cells or inject enriched medium or cells into a well of the plate, the possible contact between the tip of the nozzle and the bottom of the well being obtained by the action of said third stepper motor for adjusting the height of the plate, and in the low position, discharging into said discharge well, fixed to the lower wall of the first compartment, the aspirated impoverished medium, and proceeding to rinsing and sterilization.

In an advantageous arrangement of this embodiment, the aspiration/injection nozzle is provided with a collar projecting from its external wall which, in said low position of the aspiration/injection device, is applied by pressure against the upper edge of said discharge well for providing sealing with respect to the rinsing and sterilizing operations of the external part of the nozzle.

In an advantageous variant of this embodiment, when the device for adjusting the height of the aspiration/injection nozzle is in the intermediate position, this latter is applied, by means of said collar, against the discharge well which is contained in the same housing of the aspiration/injection device, the discharge well being carried for pivoting or sliding below the nozzle thus positioned by any appropriate means, whereas the aspiration/injection operations take place in the low position.

According to yet another advantageous embodiment of the automatic device of the invention, a separate injection device is supported by the sealing collar, integral with the nozzle of said aspiration device and comprises a sterile and hot air intake which creates a column of laminar air about the intake of nutritive medium injected through valves and which prevents the reflux of contaminating particles, namely the risks of backward contamination.

In an advantageous arrangement of this embodiment, the injection device cooperates with a device for controlling the level of the liquid medium injected into each micro-well, comprising an optical fiber carried by said collar and, below each microwell, a diode.

In another advantageous embodiment of the automatic device of the invention, it cooperates with a microprocessor for driving all the devices and controlling all the operations which they must accomplish according to the predetermined experimental protocol and which also provides, if required, data processing.

Besides the above arrangements, the invention comprises still other arrangements which will be clear from the following description.

BRIEF DESCRIPTION OF THE DRAWINGS

The invention will be better understood from the complement of description which follows which refers to the accompanying drawings in which.

It should however be understood that these drawings and the corresponding descriptive parts are given solely by way of illustration of the subject of the invention of which they form in no wise a limitation.

DESCRIPTION OF THE PREFERRED EMBODIMENTS

Figure 1:
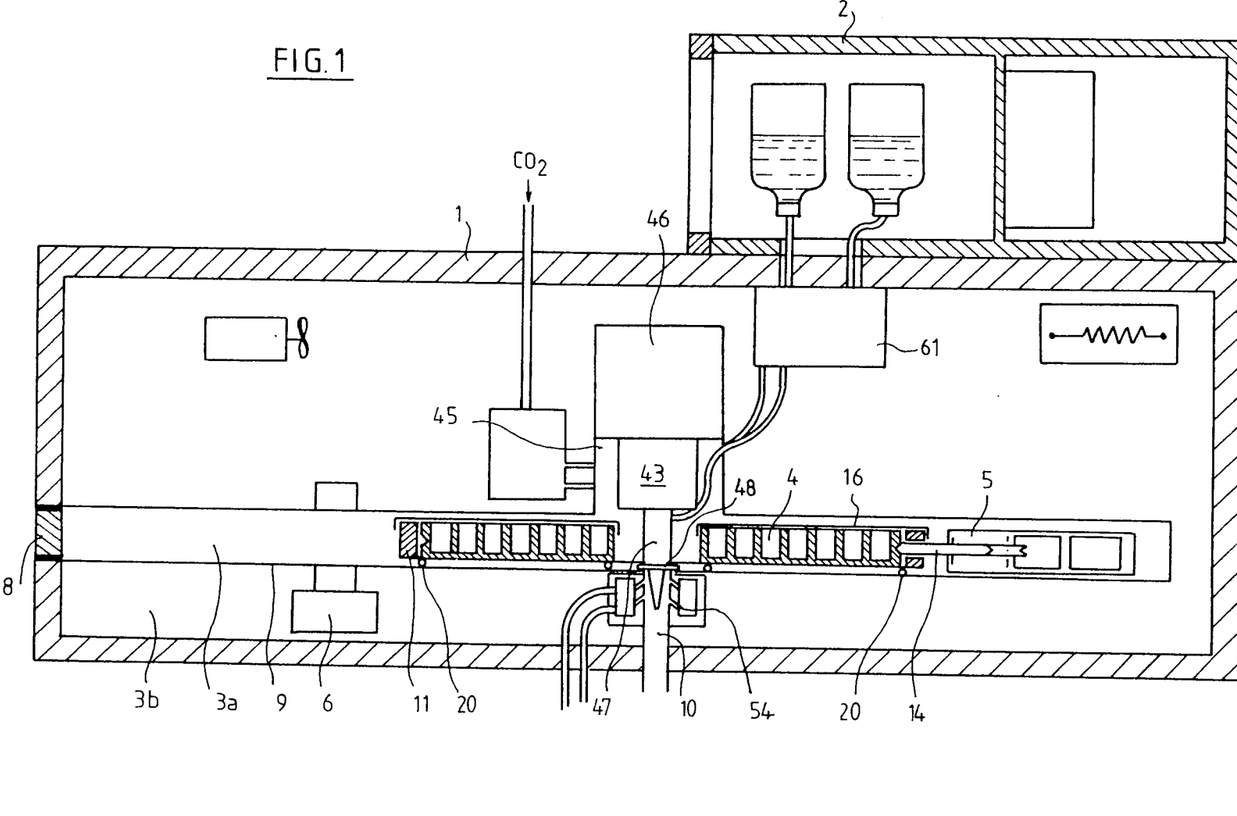
FIG. 1 shows a schematical sectional view of the apparatus of the invention.

Enclosure 1 with isolating walls is divided into two compartments;

compartment 3a, which contains a plate 4, a motor unit 5, the microscopic observation device 6 and an aspiration/injection device 7, and compartment 3b which completely surrounds the preceding one, except at the level of the access door 8 formed in the front face of enclosure 1, these compartments being separated by a metal wall 9 made from steel or an anodized aluminium, for example.

In the configuration shown in FIG. 1, a forced air flow is established between the two compartments 3a and 3b and a filter (not shown) is interposed for retaining the particles and the contamination germs.

The flow of sterile and hot air thus obtained passes through orifices (not shown) which may be formed in the bottom of compartment 3a. This flow may be taken up by orifices (not shown) which communicate with said filter. Plate 4 is made from a transparent material of good optical quality, such as polymethacrylate or glass. With an outer diameter of 25 cm, plate 4 may contain, in its external row, for example 16 microwells each having a diameter of 35 mm or else 48 microwells of 12 mm in diameter.

Plate 4 is advantageously provided with a central opening for access to said aspiration/injection device in a discharge well 10 fixed to the lower wall of the first compartment 3a.

The plate is disposed inside a sterilizable cassette 11, more especially made from metal (cf. FIG. 2), square in shape with rounded angles, which comprises a central circular recess 12 for housing plate 4.

In the rest position, this plate is held in position by support means formed preferably by four balls 21a and 21b, housed in the wall of said recess 12 and projecting therefrom for snapping into an annular groove 13 (cf. FIG. 3) formed in the side wall of plate 4. These four balls are disposed at the apices of a square inscribed in the circumference defining said circular recess 12; the two balls 21a defining the side of the square which is situated close to the motor unit 5 are fixed, whereas the two balls 21b defining the opposite side of this square are connected to a resilient spring support.

Figures 5A, 6:
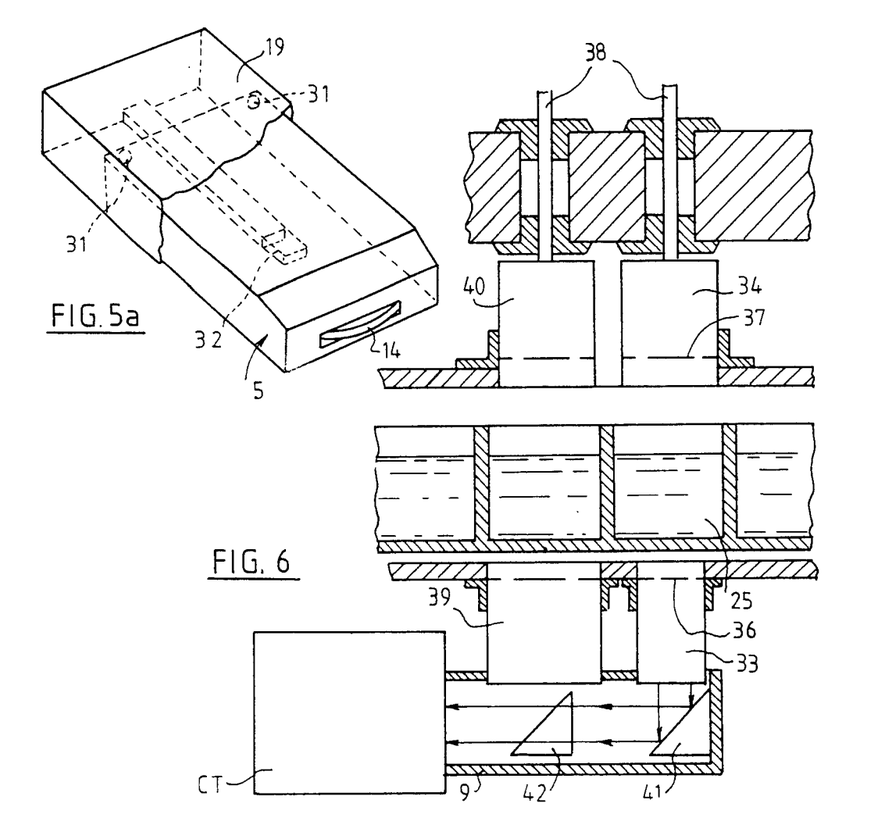
FIG. 5a also shows a perspective view of the motor unit of the invention.
FIG. 6 shows the microscopic observation device of the invention.
Figure 5B:
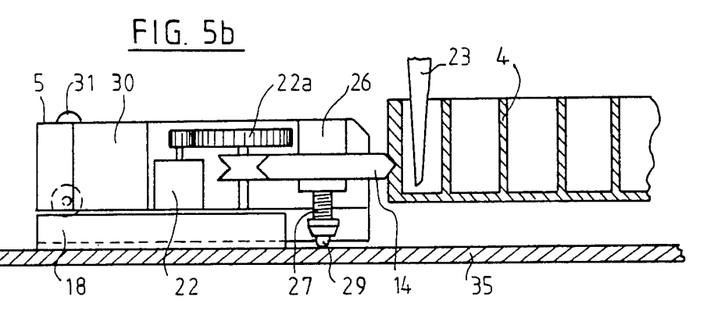
FIG. 5b shows a sectional and elevational view of the drive motor of FIG. 5, with the drive roller for rotating the plate engaged—in accordance with the invention—in the annular groove of this latter.

The rotational drive for plate 4 is obtained by friction of a drive roller 14 (cf. FIG. 5b) in groove 13 with triangular or trapezoidal profile of plate 4, in which it is engaged under the action of an electromagnet (not shown) which provides the flexible coupling between the opposite metal walls of the motor unit 5 and cassette 11: for this, a window 15 for access of roller 14 into groove 13 is provided in the middle part of the side of cassette 11 adjacent the motor unit 5. During such coupling, the engagement of the drive roller 14 in groove 13 of plate 4 pushes this latter against the two support balls 21b which are disposed opposite window 15 and on each side of the transverse axis of this latter and thus participate also in the rotational guiding of the plate, whereas the two fixed support balls 21a are freed from groove 13.

Cassette 11 is provided with a transparent lid 16 of good optical quality, fitted to said central opening in plate 4 for access of the aspiration/injection device into said discharge well 10.

This lid 16 is provided with a radial window 17 for access of this aspiration/injection device into the microwells formed in plate 4 and aligned radially.

It will be readily understood that a plurality of cassettes 11 may be provided, each comprising its own plate 4, so as to facilitate storage, particularly in a separate incubator, and so as to introduce into the first compartment 3a, through the isotherm door 8 for closing the front face of enclosure 1, only the cassette corresponding to the predetermined experimental protocol or the desired cassette.

In any case, the advantage arising from the possibility of reusing each plate after a first use should also be taken into account.

Figures 2, 3, 4:
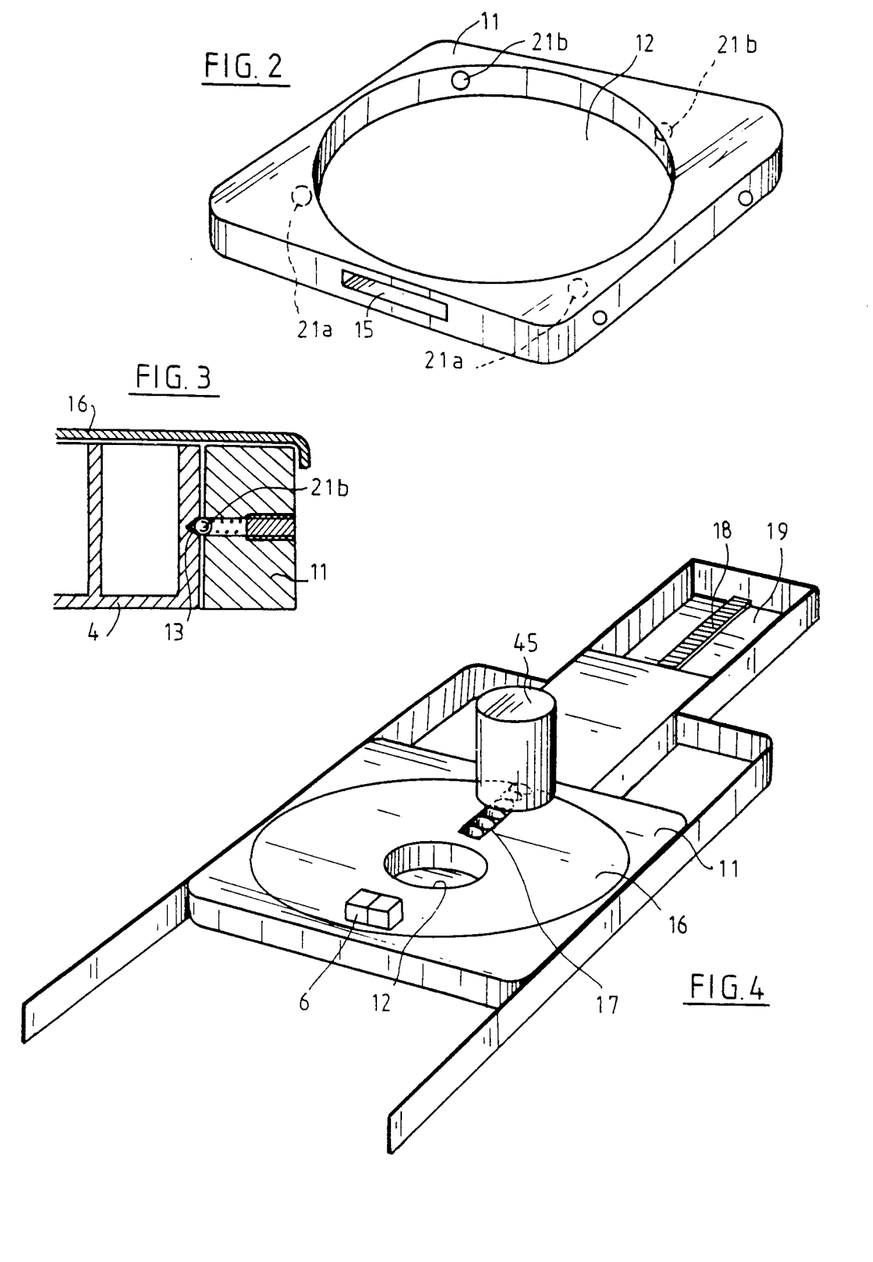
FIG. 2 is a perspective view of the cassette of the invention for supporting the plate of the invention.
FIG. 3 shows the detail of the connection between the cassette shown in FIG. 2 and the plate of the invention.
FIG. 4 shows a perspective view of the cassette with the plate and its lid and the motor unit of the invention disposed in the compartment with contains them as well as the position of the aspiration/injection and microscopic observation devices also in accordance with the invention.

Cassette 11 slides inside compartment 3a by means of balls 20 disposed on the lower wall of the cassette, as well as on its side and upper walls. FIG. 4 shows, in perspective, the configuration of compartment 3 which is designed so as to make the horizontal movements of cassette 11, with its plate 4, possible with the help of the motor unit 5, as is described further on: this FIG. 4 shows the side and lower walls of compartment 3a, the upper wall being removed for clarity of the drawing and so as to show the compartments which are contained therein; however, in this FIG. 4 can also be seen the position of the aspiration/injection device 7 and of the optical device 6 which are fixed to the upper wall of compartment 3a.

Roller 14 is actuated by a stepper motor 22 (cf. FIG. 5b) through a step down system 22a. The accuracy in the rotational positioning of plate 4 is of the order of 10 $\mu$m, i.e. of the order of the size of the cell. The frequency of motor 22 is, for example, of the order of 500 Hz and the speed of rotation of plate 4 is about 5 mm.s$^{-1}$, i.e. a complete rotation in two minutes 30 seconds. Rotation is possible in both directions.

It is sometimes necessary to vary the height of plate 4, for example for placing the needle 23 of the aspiration device 7 in contact with the cells 24 adhering to the bottom of the microwell 25 or, also, for perfecting the optical focusing knowing that the microscopic device (cf. FIG. 6) is fixed and preset. In these cases, the amplitude of the vertical movements is at most two millimeters: for this, a stepper motor 26 can be used for unilateral adjustment of the height of plate 4, which acts on a micrometric screw 27 disposed laterally with respect to said drive roller 14 and having at its lower end a ball bearing 29 sliding over the internal floor 35 separating said two compartments 3a and 3b.

Similarly, another stepper motor 30 is provided for the horizontal movements.

These three motors are connected together and form said motor unit 5.

For obtaining the horizontal movement of plate 4, taken between the drive roller 14 and balls 21b in abutting engagement, the stepper motor 30 is caused to act on a gear (not shown) projecting from the motor unit 5 and acting in its turn on a rack 18 fixed to the lower wall of housing 19 in which the motor unit 5 moves while sliding with an easy fit against the side walls of this housing 19. A recess 32 is formed in the inner part of the motor unit 5. Balls 31 also provide sliding against the upper face of housing 19.

Advantageously, the three motors 22, 26 and 30 of the motor unit 5 are of the sealed type so as to withstand the humidity which reigns in the first compartment 3a.

With the motor unit 5 of the invention, different types of sweep of the microwells 25 are possible, for example:

a sweep following a continuous plot with low magnification, or a sweep following a continuous plot with high magnification, or else a sweep following any zigzag plot.

Whereas the continuous sweeps allow densitometric profiles to be obtained, the zigzag sweeps consist of a succession of analyses of random preprogrammed fields or corresponding to individual locations.

It will be readily understood that the very principle of the automatic device allows the microwells to be automatically located by the alternation of dark zones in the densitometric profiles obtained in accordance with the plot chosen for sweeping the microwells: thus, precise resetting may be made in the case of a program error or in the case of a momentary breakdown. Furthermore, the zero of the measurements may be adjusted by darkening the bottom of a microwell or by placing optical marks.

The optical analysis of the cells contained in the microwells 25 and adhering to the bottom thereof is provided by preset lens/condenser pairs with phase contrast.

In a large number of applications, a single lens/condenser pair is required. In the example chosen, two pairs are associated and placed tangentially with respect to the circular access passing through the middle points of the microwells of the row to be analyzed, as shown in FIG. 4. Lens 33 with low magnification (10$\times$) is placed in alignment with a condenser 34 which contains the corresponding rings 36 and 37. The arrival of light into the condensers is provided by an optical fiber system 38. Similarly, the medium or high magnification lens (32$\times$ or 50$\times$) is in alignment with the condenser 40.

The two pairs 33-34 and 39-40 operate alternately. When the observation is to be made with low magnification with lens 33, an external prism (not shown) sends a light beam onto the corresponding optical fiber. The focal plane corresponds to the bottom of the microwell 25. The focusing may be modified, as explained above, by the vertical movements of plate 4. On leaving lens 33, the image is reflected by a mirror 41 to the television camera CT placed either in compartment 3b, or outside while extending the light guide g. In passing, the light rays pass through the semi-transparent mirror 42. For high magnification observation of the same cellular field, roller 14 causes plate 4 to rotate by an amount equivalent to an angular sector corresponding to the fixed pitch. With said tangential arrangement of the optical pairs, one, two or three pairs, even more, may be readily aligned and an observation device of great versatility is provided since it is not necessary to rotate the turret of a microscope for changing magnification.

Instead of using a semi-transparent intermediate mirror 42, a mirror (not shown) may be advantageously used which is retractable, more especially under the action of an electromagnet system, when the lens/condenser pair 33-34 is activated.

The optical analysis may take place visually without a camera, or with a TV camera, or with a CCD strip, or automatically by means of an image analyzer coupled to any of these image sensors.

The optical observation device 6, as well as the camera CD, are disposed outside the first compartment 3a which may be made humid without disadvantages, while protecting the condensers and the lenses by means of glass plates (not shown) embedded in the ceiling and the floor of compartment 3a at the level of the openings formed in these walls in correspondance with the position of said condensers and lenses; for this, it should be noted that the small volume of this compartment 3a provides automatic and constant humidification by evaporation of the cellular medium contained in the microwells 25.

The aspiration device 7 is of the type described in said French patent application No. 84 08839, and is formed of a piston system comprising a stepper motor and a step down system, contained in unit 43, which step down system acts on a piston contained in a cylinder 44.

The aspiration/injection device 7 is disposed in a vertical housing 45 (cf. FIGS. 1 and 4), formed in the upper wall of the first compartment 3a, and cooperates with a device 46 for adjusting the height of nozzle 47 to three positions. This device 46 may be formed by a stepper motor or by an actuating cylinder of telescopic type and allows the following operations to be carried out:

in the top position, to cause said support cassette 11 and its plate 4 to move freely;

in the intermediate position, to provide aspiration or injection, and in the low position, to remove from the discharge well the aspirated product or products.

The discharge operation may be advantageously followed by an operation for rinsing and sterilizing the external surface of nozzle 47; for this, this latter is provided with a collar 48 which allows it to be applied, in the low position, on the discharge well 10 fixed to the low wall of compartment 3a.

In some cases, it may be advantageous to mount the discharge well in housing 45 which contains the aspiration/injection device 7 and to dispose it below nozzle 47, by pivoting or sliding, by means of any means appropriate for this purpose, when this end piece is in the intermediate position, whereas the aspiration/injection operations take place in the low position; this variant is advantageous because it reduces the movements of cassette 11 which are required when the well is fixed to the bottom of compartment 3a, whenever it is desired to discharge the product or products for aligning the central opening of plate 4 with the aspiration/injection device and the discharge well.

When nozzle 47, which is made from metal, glass or a plastic material (transparent or not), and which is both a reservoir and a needle, comes into position above a housing 25, it is lowered by device 46 which is in an intermediate position (or low position) in the preceding variant. The end of the nozzle stops at about 2 mm from the bottom of housing 25.

Aspiration takes place by retraction of piston 49 (cf. FIG. 7) which sucks the membrane 50 through space 51 which, depending on the type of manipulation, may be filled with air or an inert liquid such as water or oil. The variation of space 51 allows the aspiration to be adjusted and to be made more or less energetic. The depression thus created by membrane 50 is transmitted to space 52 and sucks up the liquid contained in the micro-well 25. When the discharge well 10 is formed in the lower wall of compartment 3a, cassette 11 is moved horizontally for aligning the central opening in plate 4 with nozzle 47 and well 10. The device 46 is then brought to a low position and collar 48 is applied against the upper surface of well 10 for providing sealing. Piston 49 is then pushed back for driving out the liquid contained in 52. Through the connection 53 sterile distilled water is injected for cleaning the inside of the nozzle. Perforations 54 placed inside well 10 allow water to be injected for cleaning the outside of nozzle 46. This rinsing may be more energetic and use steam, alcohol etc . . .

After discharge and rinsing, device 46 is brought to the top position for allowing cassette 11 and plate 4 to move freely.

It will be readily understood that it is possible, using this device, to take variable amounts of liquid and replace them in microwells after having rotated plate 4. To avoid gas losses and to maintain stable conditions in compartment 3a, a valve (not shown) may close the base of well 10 and be opened through the very action of nozzle 47, of appropriate length. The shape of the end of the nozzle is bevelled. The outer diameter is about 2 mm and the central duct about 0.05 mm. By raising the plate 4 to the top position by means of said motor unit 5, the nozzle 47 and the cellular culture are brought into contact. Very reduced reciprocal movement of the plate allows the cells to be separated and to be aspirated with a view to their analysis and especially to the subculture thereof in free microwells.

Figure 7:
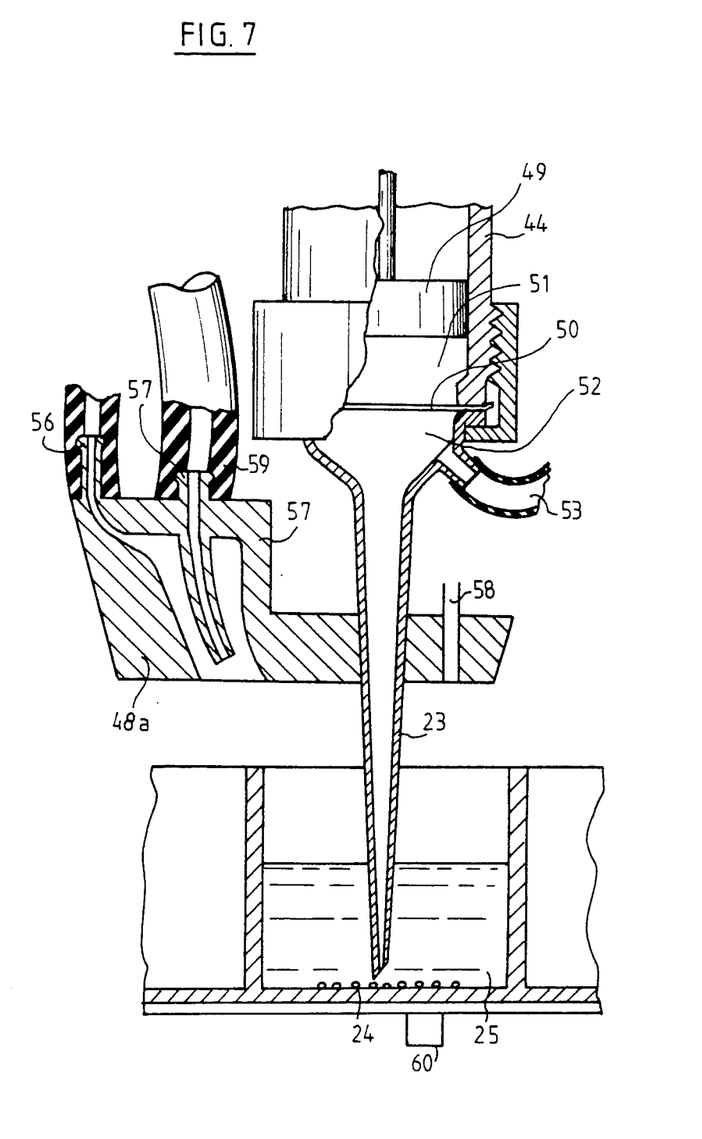
FIG. 7 shows the injection device coupled to the aspiration device of the invention.

FIG. 7 also shows how a collar 48a, of a special shape, fitted onto nozzle 47 and bonded, supports an injection device 55 separate from said aspiration device (which may in fact also be used for injection). It comprises a sterile and hot air intake 56 taken after the fan of compartment 3b. An intake 57 is provided for the injection of nutritive liquid. The air duct concentric with base 57 avoids the reflux of contaminating particles. An optical fiber 58 illuminates the microwell 25 with infrared and a diode 60 measures the light transmitted, which allows the level to be controlled. An isolating pipe 59 avoids condensation on the cold pipe which arrives at base 57.

After aspiration of the nutritive medium and before discharge thereof into well 10, the new liquids contained in the reservoir cooled by the cooled enclosure 2 (cf. FIG. 1) flow directly when constricting valves 61 (cf. FIG. 1), placed under the reservoir, open. The jet is directed against nozzle 47, which provides rinsing and avoids direct impact of the jet against the cells contained at the bottom of the microwell 25. The flow from the flask is stopped when the signal arriving at the reception diode 56 indicates a certain value which, in reality, takes into account the initial value before aspiration, the value after aspiration, then the evolution of the measurements during filling. The draining and cleaning sequence takes place as described above.

In so far as the main applications of the automatic device of the invention are concerned, they relate to:

cloning: in this case, plate 4 is disposed in cassette 11 after having seeded a single microwell 25; from the identification of the colonies, subcultures are formed and the other microwells of the plate are progressively supplied by means of said aspiration/injection device;

the analysis of the action of toxic, pharmacological or other substances: the high speed of the system of the invention allows measurements to be taken at very close intervals (of the number, of the form, of the cellular kinetics, etc . . . ), and analysis of bacteria by colorimetric reactions.

Figure 8:
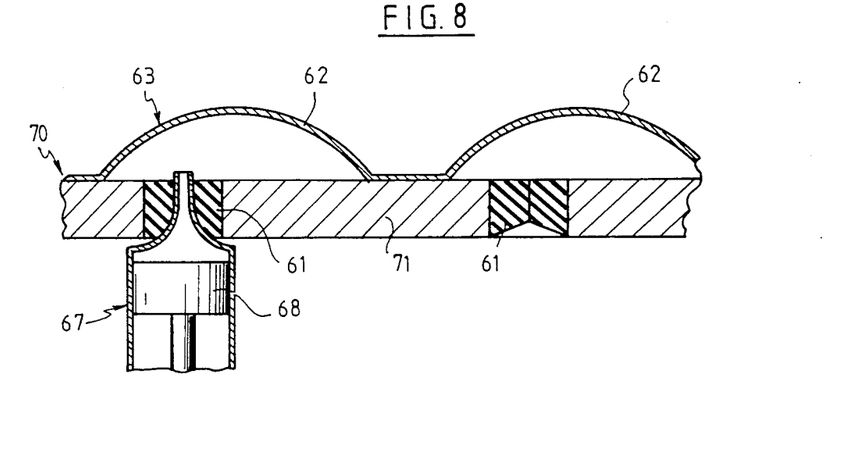
FIGS. 8 and 9 illustrate a variant of the plate in accordance with the invention.
Figure 9:
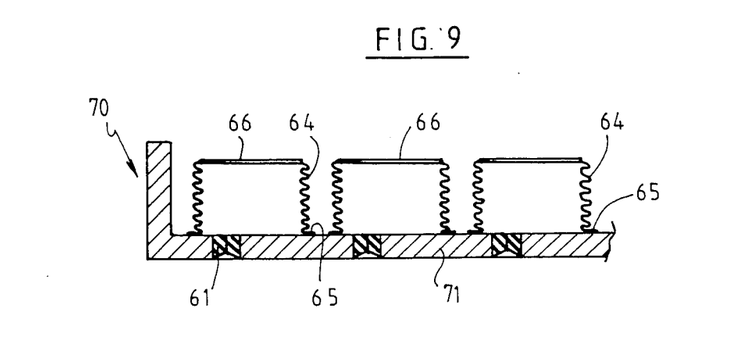

FIGS. 8 and 9 refer to a variant 70 of the above described plate which is suitable for certain applications among which may be mentioned—and this in a way which is non limitative—airborne biological experiments, namely in the presence of an environment with microgravity or a total absence of gravity (however, some experiments on Earth are also capable of being carried out by using the variant of the micro-well plate shown schematically in FIGS. 8 and 9).

In accordance with this variant, plate 70 comprises closed variable volume microwells and access of the aspiration/injection device into the inside of each microwell is provided by means of inserts 61, made more particularly from silicon elastomer, which are preperforated or perforable for passing therethrough a conventional type and more particularly metal syringe 67 which may be sterilized by heating, in particularly by means of an electric resistance incorporated in its piston (or in its cylindrical wall) or by IR heating or any equivalent means. The inserts 61 are offcentered with respect to the axis of each microwell.

FIG. 8 shows schematically a first embodiment of the variable volume micro-wells, in which the microwells are formed by microbubbles 62 substantially in the form of a spherical skull cap, which are defined by a transparent membrane 63 which is bonded to the upper face of the bottom 71 of plate 70 about each micro-bubble. In this case, the microscopic observation is made from the side of bottom 71.

FIG. 9 also shows schematically a variant of the variable volume microwells which are defined by micro-bellows 64, also made from a resilient and transparent material, which are bonded to the upper face of plate 70 about an annular collar 65 formed at the level of the lower edge of each of the micro-bellows 64, these latter being advantageously closed by transparent covers 66 having good optical qualities, which in this case allows microscopic observation to be made from the side of the micro-wells.

In some applications, the micro-bubbles and the micro-bellows may be advantageously made from a material allowing gas exchanges, namely permeable to gases.

As is clear from what has gone before, the invention is in no wise limited to those of its embodiments and modes of application which have just been described more explicitly; it embraces, on the contrary, all variants thereof which may occur to a technician skilled in the matter, without departing from the scope or spirit of the present invention.

I claim:

1. An automatic device for analyzing and cloning cellular cultures as well as for bacteriological analysis, comprising:
    a first enclosure having isolating walls and divided into a first compartment and a second compartment surrounding the first compartment;
    at least one microscopic device for observation of said cultures, which is integral with a ceiling and a floor of said first compartment,
    access means for accessing an interior of said first compartment;
    support means for supporting said first compartment within said second compartment;
    a device for aspiration/injection of cell medium or cells fixed to a housing formed in said ceiling of said first compartment;
    a plate including several micro-wells for receiving said cellular cultures and cell medium, said microwells being disposed in at least one concentric circular row, means for slidably supporting said plate inside said first compartment, said plate being provided with a central opening for access of said aspiration/injection device into a discharge and sterilization well fixed to the floor of said first compartment;
    drive means located in said first compartment and comprising means for rotating said plate and means for moving said plate vertically and horizontally to thus orientate each micro-well with respect to said microscopic device;
    means for providing homeothermic conditions inside said enclosure,
    a second enclosure, disposed outside said first enclosure, said second enclosure including a plurality of reservoirs for containing nutritive media in one reservoir and at least one other product in at least one other reservoir, cooling means for preserving the contents of said reservoirs means, and means for selectively supplying said nutritive media and said at least one other product to said aspiration/injection device by means of valve means.

2. The automatic device as claimed in claim 1, wherein said first compartment comprises filtering walls, and wherein said second compartment further comprises means for providing in said first compartment a flow of filtered laminar air through said filtering walls.

3. The automatic device as claimed in claim 2, wherein said plate is circular and further comprises an annular groove formed in an outer wall thereof, wherein the means for slidably supporting said plate includes a cassette provided with sliding means integral with walls thereof, a central circular recess for housing said plate, at least four balls housed in a vertical wall of said recess and projecting therefrom for snapping into the annular groove of said plate and a window made in a vertical wall thereof opposite said drive means, and wherein said drive means includes a drive roller projecting from a motor and means for frictionally engaging said drive roller with said annular groove through the window of said cassette.

4. The automatic device as claimed in claim 3, wherein two of said balls are fixed, whereas the other two balls are on a resilient support, these four balls being disposed at the apices of a square inscribed in the vertical wall of said circular recess, one side of the square, parallel and contiguous to said access window for the drive roller, being defined by the two fixed balls, whereas the opposite side of the square is defined by said two balls on said resilient support, said mans for frictionally engaging said drive roller with said annular groove thus pressing said plate against said two balls on said resilient support, while releasing said plate from said two fixed balls.

5. The automatic device as claimed in claim 3, wherein said means for engaging the drive roller in the groove of said plate are formed by an electro-magnet providing flexible coupling between opposite metal walls of the drive means and the cassette.

6. The automatic device as claimed in claim 3, wherein the cassette is provided with a transparent lid, of good optical quality, fitted to said central opening of the plate and having a radial window for access of said aspiration/injection device into the micro-wells of said plate.

7. The automatic device as claimed in claim 3, wherein said sliding means comprise balls disposed on the side walls and on lower and upper walls of the cassette to thereby allow the free sliding of said cassette.

8. The automatic device as claimed in claim 3, wherein said cassette, said plate and said lid are made of sterilizable material.

9. The automatic device as claimed in claim 1, wherein said plate is circular and further comprises an annular groove formed in an outer wall thereof, wherein the means for slidably supporting said plate includes a cassette provided with sliding means integral with walls thereof, a central circular recess for housing said plate, at least four balls housed in a vertical wall of said recess and projecting therefrom for snapping into the annular groove of said plate and a window made in a vertical wall thereof opposite said drive means, and wherein said drive means includes a drive roller projecting from a motor, and means for frictionally engaging said drive roller with said annular groove through the window of said cassette.

10. The automatic device as claimed in claim 9, wherein two of said balls are fixed, whereas the other two balls are on a resilient support, these four balls being disposed at the apices of a square inscribed in a vertical wall of said circular recess, one side of the square, parallel and contiguous to said recess window for the drive roller, being defined by the two fixed balls, whereas the opposite side of the square is defined by said two balls on said resilient support, said means for frictionally engaging said drive roller with said annular groove thus pressing said plate against said two balls on said resilient support, while releasing said plate from said two fixed balls.

11. The automatic device as claimed in claim 9, wherein said means for engaging the drive roller in the groove of said plate are formed by an electro-magnet providing flexible coupling between opposite metal walls of the drive means and the cassette.

12. The automatic device as claimed in claim 9, wherein the support cassette is provided with a transparent lid, of good optical quality, fitted to said central opening of the plate and having a radial window for access of said aspiration/injection device into the micro-wells of said plate.

13. The automatic device as claimed in claim 9, wherein said sliding means comprise balls disposed on side walls and on lower and upper walls of the cassette to thereby allow the free sliding of said cassette.

14. The automatic device as claimed in claim 9, wherein said cassette, said plate and said lid are made of sterilizable material.

15. The automatic device as claimed in claim 1, wherein said drive means comprises in combination:
a first stepper motor for rotating said plate, which acts on said drive roller through a step down system,
a second stepper motor for horizontally moving said plate by acting on a gear system which projects from said motor unit and which in its turn acts on at least one rack fixed to the floor of said first compartment, and
a third stepper motor for unilateral adjustment of the height of said plate, which acts on a micrometric screw disposed laterally with respect to said drive roller and having at its lower end a ball bearing sliding over the floor of said first compartment, thus allowing the horizontal movements controlled by said second stepper motor.

16. The automatic device as claimed in claim 1, wherein said microscopic observation device comprises two preset lens/condenser pairs which are associated together for operating alternately, the first and second condensers and the first and second lenses being integral with the ceiling and the floor, respectively, of the first compartment, which first lens is of low magnification, whereas the second lens provides medium or high magnification, the arrival of light into said two condensers taking place through an optical fiber system.

17. The automatic device as claimed in claim 16 wherein each lens cooperates with a mirror and an image sensor defined by a television camera or a CCD strip.

18. The automatic device as claimed in claim 17 wherein the intermediate mirror, which is interposed between said image sensor and the mirror the furthest away from this latter, is semi-transparent.

19. The automatic device as claimed in claim 17, wherein said intermediate mirror is retractable, under the section of an electromagnet means, when the lens/condenser pair furthest away from the image sensor is activated.

20. The automatic device as claimed in claim 1, wherein said aspiration/injection device cooperates with a device for adjusting, to three positions, the height of the aspiration/injection nozzle, said adjusting device being defined by a stepper motor or by a telescopic actuating cylinder, whereby:
in the high position, the cassette as well as the plate are freely movable,
in the intermediate position, the impoverished cellular medium or cells is aspiratable from, or enriched medium or cells are injectable into a well in said plate, and the tip of said nozzle being capable of contacting the bottom of the well by the action of said third stepper motor adjusting the height of the plate, and
in the low position, the impoverished aspirated medium is dischargable into said discharge well, fixed to the lower wall of said first compartment, and rinsing and sterilization may be carried out.

21. The automatic device as claimed in claim 20, wherein the aspiration/injection nozzle is provided with a collar projecting from its external wall which, in said low position of the aspiration/injection device, is applied by pressure against the upper edge of said discharge well for providing sealing with respect to rinsing and sterilizing for the external part of the nozzle.

22. The automatic device as claimed in claim 20, wherein, when the device for adjusting the height of the aspiration/injection nozzle is in the intermediate position, this latter is applied, by means of said collar, against the discharge well which is contained in the same housing of the aspiration/injection device, said discharge well being brought by pivoting or sliding below the nozzle thus positioned, whereas the aspiration/injection operations take place in the low position.

23. The automatic device as claimed in claim 20, wherein said injection device is supported by said sealing collar, fixed to the nozzle of said aspiration device, and comprises a sterile and hot air intake which creates a column of laminar air about the intake of nutritive medium injected through valves, and which prevents reflux of contaminating particles.

24. The automatic device as claimed in claim 23, wherein said injection device cooperates with a device for controlling the level of the liquid medium injected into each said micro-well, said controlling device comprising an optical fiber carried by said collar and, below each said micro-well, a diode.

25. The automatic device as claimed in claim 1, further comprising a microprocessor including means for controlling all the operations of said automatic device, as well as means for processing data from said automatic device.

26. The automatic device as claimed in claim 1, wherein said plate comprises micro-wells which are closed and have a variable volume, access of said aspiration/injection device into an interior of each micro-well being provided by a preperforated or perforable insert, made from silicon elastomer, each insert being positioned in a bottom of said plate and being disposed eccentrically with respect to a central vertical axis of the corresponding micro-well, said bottoms of said micro-wells being transparent and of good optical quality.

27. The automatic device as claimed in claim 26, wherein said variable volume micro-wells are formed by microbubbles substantially in the form of a spherical skull cap, which are defined by a transparent resilient membrane bonded to an upper face of said plate.

28. The automatic device as claimed in claim 26, wherein said variable volume micro-wells are formed by microbellows made from a resilient and transparent material which are bonded to an upper face of the plate about an annular collar formed at lower edges of said micro-bellows.

29. The automatic device as claimed in claim 28, wherein said microbellows are each closed by a transparent cover having good optical qualities and which is fixed to side walls of the micro-bellows.

30. The automatic device as claimed in claim 27, wherein said micro-bubbles are made from a gas permeable resilient material.

31. The automatic device as claimed in claim 26, wherein said aspiration/injection device is formed by a heat-sterilizable metal syringe and sterilizing means are contained within said automatic device.

32. The automatic device as claimed in claim 1, wherein said circular plate is placed in a cassette, more especially made from metal and substantially square in shape which, when it is equipped with a lid, has a configuration close to that of the Petri box for reducing risks of contamination and which comprises a central circular recess housing said plate which, in the rest position, is held in position by support means preferably formed by four balls housed in the wall of said recess and projecting therefrom for snapping into an annular groove formed in the outer wall of said plate, whereas the rotational drive of the plate is provided by means of a drive roller, proejcting from said motor unit by engagement, under the action of appropriate means, and by friction in said groove of said plate, for this purpose an access window of the roller into said groove is formed in the middle part, on the same side of the cassette adjacent the motor unit.

* * * * *

UNITED STATES PATENT AND TRADEMARK OFFICE
CERTIFICATE OF CORRECTION

PATENT NO.   : 4,800,164
DATED        : January 24, 1989
INVENTOR(S)  : Jean-Claude BISCONTE It is certified that error appears in the above-identified patent and that said Letters Patent is hereby corrected as shown below:

On the title page, item [73], should read
--[73] Assignee: Jean-Claude Bisconte , Paris France--

Signed and Sealed this

Twenty-eighth Day of November 1989

*Attest:*

JEFFREY M. SAMUELS

*Attesting Officer*   *Acting Commissioner of Patents and Trademarks*